(12) United States Patent
Koster et al.

(10) Patent No.: US 8,313,785 B2
(45) Date of Patent: Nov. 20, 2012

(54) LIQUID YEAST COMPOSITIONS

(75) Inventors: Frans Koster, Delfgauw (NL); Unno Adrianus De Vreede, Berkel en Rodenrijs (NL)

(73) Assignee: Lesaffre et Compagnie, Paris (FR)

( * ) Notice: Subject to any disclaimer, the term of this patent is extended or adjusted under 35 U.S.C. 154(b) by 2513 days.

(21) Appl. No.: 10/497,666

(22) PCT Filed: Nov. 28, 2002

(86) PCT No.: PCT/EP02/13480
§ 371 (c)(1),
(2), (4) Date: Jan. 3, 2005

(87) PCT Pub. No.: WO03/048342
PCT Pub. Date: Jun. 12, 2003

(65) Prior Publication Data
US 2005/0129808 A1    Jun. 16, 2005

(30) Foreign Application Priority Data
Dec. 5, 2001 (EP) ................................. 01204783

(51) Int. Cl.
*A23L 1/28* (2006.01)
(52) U.S. Cl. .......................................... 426/62; 426/656
(58) Field of Classification Search .................. 426/656, 426/62
See application file for complete search history.

(56) References Cited

U.S. PATENT DOCUMENTS

| | | | |
|---|---|---|---|
| 2,947,668 A * | 8/1960 | Kuestler et al. ................ | 426/62 |
| 3,843,800 A | 10/1974 | Langejan | |
| 4,405,650 A | 9/1983 | Spadafora | |
| 4,764,472 A | 8/1988 | Pomper et al. | |
| 5,707,669 A | 1/1998 | Soltis et al. | |

FOREIGN PATENT DOCUMENTS

| | | |
|---|---|---|
| EP | 616030 | 9/1994 |
| EP | 659344 | 6/1995 |
| EP | 821057 | 1/1998 |
| EP | 461725 | 7/2003 |
| GB | 1135418 | 11/1966 |
| JP | 45-32235 | 10/1970 |
| JP | 45032235 | 10/1970 |
| JP | 10-127274 | 5/1998 |
| WO | WO 91/12315 | 8/1991 |
| WO | WO 91/18513 | 12/1991 |
| WO | WO 01/47363 | 7/2001 |
| WO | WO 01/83309 | 11/2001 |
| WO | WO 02/02428 | 1/2002 |
| WO | WO 02/33048 | 4/2002 |
| WO | WO 02/49441 | * 6/2002 |

OTHER PUBLICATIONS

International Search Report for PCT/EP02/13480, mailed on Apr. 28, 2004, 3 pages.
Reed and Nagodawithana, Yeast Technology, 2$^{nd}$ ed., (1991) pp. 261-314.
Notice of Opposition to (Lesaffre et Compagnie) European Patent 1450613, filed Sep. 30, 2010.
Notice of Opposition (Lallemand SAS) to European Patent 1450613, filed Sep. 29, 2010.
Logothetis et al. "Effect of salt hyperosmotic stress on yeast cell viability" Proc. Nat. Sci. Matica Srpska Novi Sad 113:271-284 (2007).
White "Some aspects of yeast physiology" in *Yeast Technology*, Chapman & Hall, Chapter XIII, pp. 162-167 (1954).

* cited by examiner

*Primary Examiner* — D Lawrence Tarazano
*Assistant Examiner* — Hamid R Badr
(74) *Attorney, Agent, or Firm* — Nixon & Vanderhye P.C.

(57) ABSTRACT

The present invention provides a composition comprising between 24% and 45% yeast (based on yeast dry matter content) characterized in that it contains more than 0.75% salt; and that the composition is liquid; and that the composition is biologically stable by maintaining the composition below 10° C.

13 Claims, 1 Drawing Sheet

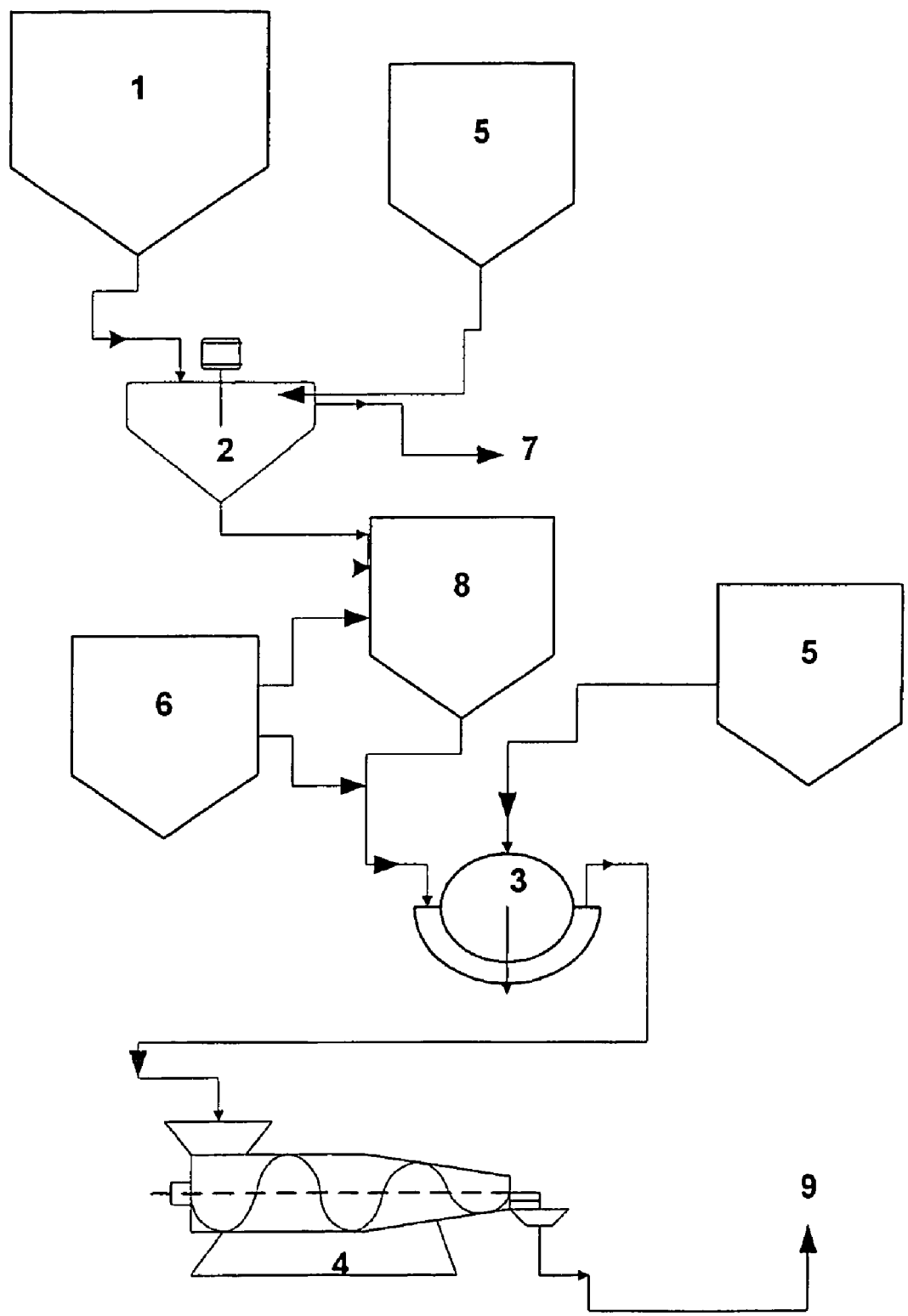

LIQUID YEAST COMPOSITIONS

CROSS-REFERENCE TO RELATED APPLICATIONS

This application is the national stage of PCT application PCT/EP02/13480 having an international filing date of 28 Nov. 2002, which claims priority from European application 01204783.3, filed 5 Dec. 2001. The contents of these documents are incorporated herein by reference.

The present invention relates to a liquid yeast composition, to a process for the preparation said liquid yeast composition, to processes for preparing dough and baked products using said liquid yeast composition and to a process for storing said liquid yeast composition.

The production of baker's yeast is well known and amply documented in the literature. A good example of a description of the production of baker's yeast can be found in Reed, G. and Nagodawithana, T. W. (1991) Yeast Technology, $2^{nd}$ ed., pp 261-314, Van Nostrand Reinhold, New York and is schematically represented in FIG. 1.

After the fermentation process the yeast cells are washed thoroughly by repeated concentration and dilution with water in order to obtain a yeast composition with a yeast dry matter content of 17 to 23% which is known in the art as cream yeast (or yeast cream or cream of baker's yeast). Cream yeast may be sold as such or may be further processed into compressed yeast or granulated yeast with a yeast dry matter content of 27 to 34%, or dried further to obtain active dry yeast (ADY) or instant dry yeast (IDY) with a yeast dry matter content of 90 to 97%.

The quantity of water that is removed from the fermentation broth amounts to about 50% for cream yeast and up to almost 100% for dried yeast. Together with the water required to wash the yeast cells, this water forms a large stream of wastewater that needs to be handled in a wastewater treatment plant. These efforts will increase in the future as demands for treatment of waste streams increase for environmental reasons.

Yeast cells contain a considerable amount of intracellular water; approximately 65% of the cell weight is intracellular water and 35% constitutes yeast dry matter. Depending on the yeast dry matter content of a given yeast composition, this leads to liquid, pasty or solid behavior is as summarized in Table 1. A consequence of the large fraction of intracellular water (ca 65%) is that, depending on the yeast dry matter content, the amount of extracellular water in the yeast composition is low and that solidification at already low yeast dry matter contents may occur.

The industrial solid yeast compositions currently available, so-called compressed yeast, have dry yeast matter contents of 27 to 34%. This type of yeast cannot be used in automatic dosing systems but instead has to be crumbled prior to its use.

TABLE 1

| Product | Yeast dry matter content (A) | Intracellular water (65/35 * (A)) (B) | Extracellular water (100 − (A) − (B)) | Physical state |
|---|---|---|---|---|
| Cream yeast | 17% | 32% | 51% | liquid |
|  | 20% | 37% | 43% | liquid |
|  | 23% | 43% | 34% | liquid |
| Yeast paste | 25% | 46% | 29% | pasty |
| Compressed yeast | 27% | 50% | 23% | solid |
|  | 30% | 56% | 14% | solid |
|  | 34% | 63% | 3% | solid |

In order to overcome these problems, cream yeast may be used since it permits the baker to add the yeast directly into the mixers by automatic dosing systems. Furthermore, the use of cream yeast eliminates several processing steps at the yeast production plant.

However, a major drawback of the use of the traditional type of cream yeast is the amount of extra water that has to be transported in comparison with the more concentrated solid yeast compositions. In practice, the exchange rate between cream yeast and compressed yeast is approximately 1.5 which means that 1.5 kg of cream yeast is required to replace 1 kg compressed yeast in order to have the same fermentative (leavening) activity. Another problem associated with cream yeast is the well-known sedimentation problem. In practice, this problem may be solved by stabilizing the cream yeast as disclosed in EP-A-461725 or stirring the cream yeast as is described in NL259948.

Therefore, there is an urgent need for liquid yeast compositions with yeast dry matter contents higher than cream yeast (i.e. having a yeast dry matter content of more than 23%) such that useless shipping of water can be prevented.

WO 91/12315 describes addition of polyols to salt-free fresh yeast in order to obtain a higher dry matter yeast liquid with all the advantages of liquid yeast in industrial baking. With high amounts of glycerol a liquid preparation is made for better performance in frozen dough processes. Using glycerol, it is described to prepare liquid yeast compositions with a yeast dry matter content up to a maximum of 29%. Unfortunately, the use of glycerol is accompanied with several major disadvantages. First of all, glycerol is very expensive in the concentration ranges used. Secondly, we have found that the yeast cells take up glycerol with the unwanted side effect that the yeast preparation turns back into a pasty or even solid preparation.

In the context of the present invention, the term "yeast" relates to living yeast cells such as from the genera *Saccharomyces, Kluyveromyces, Torulospora*, in particular *Saccharomyces cerevisiae* or *Torulaspora delbrueckii*. The term also comprises combinations of one or more yeast species optionally with other microorganisms such as lactic acid bacteria. Preferably the yeast is baker's yeast or *Saccharomyces cerevisiae*.

Cream yeast is defined as the yeast composition obtained after fermentation and subsequent concentration and washing of the cells according to known methods resulting in a yeast composition with a yeast dry matter content from 17% to 23% (wt %).

Biologically stable is defined herein as the property of the yeast comiposition of the invention to maintain more than 90% of its leavening activity when kept for 10 days at a temperature below 10° C., measured in a lean dough system.

Processing aids are defined herein as compounds that improve the handling properties of the dough and/or the final properties of the baked products. Dough properties that may be improved comprise machineability, gas retaining capability, and etcetera. Properties of the baked products that may be improved comprise loaf volume, crust crispiness, crumb texture and softness and shelf life. These dough and/or baked product improving processing aids can be divided into two groups: chemical additives and enzymes.

The term liquid is used to describe a physical state that is fluid without being gaseous so as to flow freely typically in the manner of water and to have a definite volume without having a definite shape except such as is temporarily given by a container.

Salt content is defined as the amount of salt expressed as weight percentage of the total weight of the preparation including water.

The present invention provides a yeast composition, which comprises from 24% to 45% yeast (based on dry yeast matter content) and more than 0.75% salt whereby the composition is liquid and biologically stable by maintaining the composition at a temperature below 10° C. The present invention further provides processes for the production of the yeast composition of the invention, the production of dough using said liquid yeast composition as well as baked products from said dough. The invention also provides a process for storing the liquid yeast composition of the invention.

In a first aspect of the invention, there is provided a yeast composition comprising from 24% to 45% yeast (based on yeast dry matter content) characterized in that it contains more than 0.75% salt, that the composition is liquid and that it is biologically stable by maintaining the composition at a temperature below 10° C. Preferably, the temperature of the composition of the present invention is kept ≦8° C., more preferably ≦6° C. and even more preferably ≦4° C.

The advantage of the present invention is that the yeast composition has a yeast dry matter content which is higher compared with normal cream yeast (17-23%) and comparable to or even exceeding the yeast dry matter content of compressed yeast (27-34%). It therefore combines the advantage of traditional compressed yeast (high yeast dry matter content) with the advantage of traditional cream yeast (ease of operation). Another important advantage is that the composition of the invention is biologically stable with respect to its leavening activity (see definition above). Thus, the compositions of the invention allow not only convenient production and storage by the yeast manufacturer but they can also easily be transported to and conveniently stored and used by the baker. The compositions of the present invention may be used directly, without prior pretreatment such as warming up, for the manufacturing of leavened dough of any type. The compositions of the present invention are suitable for not only large industrial bakers but also for the smaller bakeries or artisanal bakers. In addition, the composition of the present invention adds the advantages of salt disposal reduction at the yeast manufacturer and, in particular in case sodium chloride is used, decreases the salt addition of the baker when making dough and/or baked products. In comparison with traditional cream yeast, the liquid yeast compositions of the present invention display, depending on their salt content, an improved resistance against microbial infections. Also, there is a lesser tendency of the yeast cells to sediment, which reduces the need for homogenization by stirring (e.g. NL 259948) or adding stabilizers agents such as (xanthan) gum (e.g. EP-A-461725).

In JP45-32235, liquid yeast compositions are disclosed that are made from compressed yeast by adding a combination of one or more sugars and one or more salts. The aim of the inventors resided in providing a liquid yeast composition that has almost no gas production by fermentation or autofermentation at room temperature, with a dough expanding power that continues during a long time, and without sedimentation of the yeast, even when it is left standing still. According to this document, the simultaneous presence of both salts and sugars was a prerequisite in order to establish biological stability at elevated temperatures.

For the liquid yeast compositions of the present invention, the amount of salt may be chosen in such a way that the composition is liquid at the desired yeast dry matter. For example, a liquid yeast composition with a yeast dry matter content of approximately 26% can be obtained using sodium chloride at a concentration of 1 wt %; a liquid yeast composition with a yeast dry matter content of approximately 35% can be obtained using sodium chloride at a concentration of 10 wt %. When sodium chloride concentrations around 5 wt % were applied, it was possible to obtain yeast liquid compositions with a yeast dry matter content of approximately 30%, which is in the same range as the standard compressed yeast products (27-33%). The skilled person will understand that other suitable combinations of salt and dry yeast matter content and/or other salts or combinations of salts can be determined easily at yeast dry matter contents within the range of 24% to 45% by simple extrapolation and a few experiments.

The yeast dry matter content of the liquid yeast compositions of the invention may be between 24 and 45%. Preferred embodiments of the invention comprise yeast dry matter contents of ≧24%, or ≧25%, or ≧26% or ≧27% or ≧28% or ≧29% or ≧30% or ≧31% or ≧32% or ≧33% or ≧34% or ≧35% while the yeast dry matter content is preferably ≦45% or more preferably ≦40%.

The salt content is preferably more than 0.75% and not more than 10%. More preferably the salt content is ≧1% or ≧2% or ≧3% or ≧4% or ≧5%, or ≧6% or ≧7% or ≧8% or ≧9% and not more than 10%. Preferred salts are alkaline or earth-alkaline metal salts or ammonium salts or combinations thereof. More preferably the salts are lithium, sodium, potassium, magnesium, calcium or ammonium salts or combinations thereof. Most preferably the salt is sodium chloride.

The liquid yeast compositions may contain between 0 and 1% (wt %) of a sugar such as sucrose, glucose or any other mono- or disaccharide. Preferably, no such sugars are added so that the liquid yeast compositions do not comprise any of said sugars.

In yet another preferred embodiment of the invention, processing aids as defined above, are added to the liquid yeast composition of the present invention. These processing aids may be chemical additives and/or enzymes. Chemical additives and/or enzymes are added to the compositions of the invention in such an amount that the properties of the dough and/or of the baked product thereof, are improved when said compositions are added to the dough compared to no addition of said processing aids.

Suitable chemical additives are oxidizing agents such as ascorbic acid, bromate and azodicarbonamide and/or reducing agents such as L-cysteine and glutathione. A preferred oxidizing agent is ascorbic acid, which is added to the composition in such amounts that result in an amount between 5 and 300 mg per kg flour. Other suitable chemical additives are emulsifiers acting as dough conditioners such as diacetyl tartaric esters of mono/diglycerides (DATEM), sodium stearoyl lactylate (SSL) or calcium stearoyl lactylate (CSL), or acting as crumb softeners such as glycerol monostearate (GMS) or bite salts, fatty materials such as triglycerides (fat) or lecithin and others. Preferred emulsifiers are DATEM, SSL, CSL or GMS. Preferred bile salts are cholates, deoxycholates and taurodeoxycholates.

Suitable enzymes are starch degrading enzymes, arabinoxylan- and other hemicellulose degrading enzymes, cellulose degrading enzymes, oxidizing enzymes, fatty material splitting enzymes, protein degrading enzymes. Preferred starch degrading enzymes are endo-acting amylases such as alpha-amylase and exo-acting amylases such as beta-amylase and glucoamylase. Preferred arabinoxylan degrading enzymes are pentosanases, hemicellulases, xylanases and/or arabinofuranosidases, in particular xylanases from *Aspergillus* of *Bacillus* species. Preferred cellulose degrading enzymes are cellulases (i.e. endo-1,4-beta-glucanases) and cellobiohydrolases, in particular from *Aspergillus, Trichoderma* or *Humicola* species. Preferred oxidizing enzymes are lipoxygenases, glucose oxidases, sulfhydryl oxidases, hexose oxidases, pyranose oxidases and laccases. Preferred fatty material splitting enzymes are lipases, in particular fungal lipases from *Aspergillus* or *Humicola* species, and phospholipases such as phospholipase A1 and/or A2. Preferred protein-degrading enzymes are endo-acting proteinases such as those belonging to the classes thiolproteases, metalloproteases, serine proteases and aspartyl proteases, as well as exo-acting proteinases, also referred to as peptidases, belonging to the class of aminopeptidases and carboxypeptidases. The enzymes may originate from animal, plant or microbial origin and they may be obtained from these sources by classical processes known in the art, or, alternatively, they may be produced via recDNA technology. A preferred production process comprises fermentation processes in which fungi, yeast or bacteria are grown and produce the desired enzymes, either inherently or as a result of genetic modification (recDNA technology). These processes are well known in the art. Preferably, the enzymes are secreted by the microorganisms into the fermentation broth. At the end of the fermentation process, the cell biomass is usually separated and, depending on the enzyme concentration in the broth, the latter may be concentrated further and optionally washed by known techniques such as ultrafiltration. Optionally, the enzyme concentrates or a mixture of such concentrates may be dried by known techniques such as spray drying.

Other compounds that may be incorporated in the liquid yeast composition of the present invention are those that lead to easier and more accurate dosing of said composition and/or to easier and more hygienic cleaning of the dosing equipment and/or, very importantly, better and more homogeneous mixing with the basic dough ingredients flour and water and therefore to a more efficient use of the yeast and the processing aids referred to above.

In still another embodiment of the invention, gums or other non-fermentable thickening agents may be added to the liquid yeast composition as stabilizing compounds to further prevent or suppress sedimentation of the yeast cells.

The second aspect of the invention relates to a process for the production of the composition of the invention as defined in the first aspect. The process comprises the following steps:
a) preparing a yeast suspension with a yeast dry matter content between 3% and 23%;
b) concentrating the yeast suspension of step a) to a yeast composition with a yeast dry matter content higher than 23%;
c) adding solid salt or a salt solution to the yeast suspension during or after any of steps a) or during step b) or to the yeast composition during or after step b); and
d) cooling the yeast suspension or composition before, during or after step c) to a temperature below 10° C.

In one embodiment, the yeast suspension prepared in step a) may be a fermentation broth as can be obtained by commonly known processes such as those described in Reed, G. and Nagodawithana, T. W. (1991) Yeast Technology, $2^{nd}$ ed., pp 261-314, Van Nostrand Reinhold, New York. The dry yeast matter content of a typical fermentation process is in the order of 4-8% and salt(s) may already be present in a concentration between 0.5% and 2%. In such a case, solid salt or a salt solution may be added during the actual fermentation process or to the final fermentation broth. The addition of said salt may be such that upon further concentration and optionally washing the fermentation broth with water and/or a salt solution, the liquid yeast composition of the invention with a desired dry yeast matter content of more than 23% may be obtained directly. Alternatively, a fermentation broth can be used with an already higher yeast dry matter content (i.e. >8%) such as those that are disclosed in EP-A-0821057 or WO02/33048.

In a second embodiment, the fermentation broth as obtained above, may first be concentrated and washed in order to obtain an intermediate yeast suspension with a yeast dry matter around 9-11% according to methods known in the art. Solid salt or a salt solution may be added as above or during or after the production of the intermediate yeast suspension in such a way as to obtain, after further concentration and optionally washing of the intermediate yeast suspension with water and/or a salt solution, the liquid yeast composition of the invention with the desired dry yeast matter content.

In a third embodiment, the fermentation broth as obtained above, may first be concentrated and washed in order to obtain cream yeast with a yeast dry matter content around 17-23%. Solid salt or a salt solution may be added as above or during or after the production of cream yeast in such a way as to obtain, after further concentration and optionally washing of the cream yeast with water and/or a salt solution, the liquid yeast composition of the invention with the desired dry yeast matter content.

In a fourth embodiment, the fermentation broth, or the intermediate yeast suspension or the cream yeast as obtained before, may be concentrated further in order to obtain yeast cake according to methods known in the art. Solid salt or a salt solution may be added during the actual fermentation process or to the final fermentation broth, or during or after the production of the intermediate yeast suspension or during or after the production of cream yeast, or prior to or during extrusion and/or after extrusion to the yeast cake in such a way as to obtain the liquid yeast composition of the invention with the desired dry yeast matter content.

In a fifth embodiment, the yeast cake as obtained above may be dried further using known techniques in order to obtain active dried yeast (ADY) or instant dried yeast (IDY) according to known methods. These dried yeast compositions may in turn be used as a starting material for the production of the liquid yeast composition of the invention by the addition of a salt solution in such a way that a desired dry yeast matter content is obtained.

In a sixth embodiment, the yeast suspension of step a) with a yeast dry matter content between 3 and 23% may also be prepared by resuspending yeast cake or compressed yeast or by rehydrating and resuspending ADY or IDY. The liquid yeast composition of the invention may then be obtained by adding of salt or a salt solution to the yeast suspension followed by further concentration and optionally washing of the yeast suspension with water and/or a salt solution, in such a way that the liquid yeast composition of the invention with the desired dry yeast matter content is obtained.

Concentration of the yeast suspensions or compositions as described above, may be carried out using any suitable solid/liquid separation technique, preferably centrifugation and/or filtration. Although any centrifugation equipment is suitable for carrying out the process, preferred centrifugation equipment comprises a disc stack separator. Salt can be added at any point of the process. The salt can be added in solid form or as a solution.

In another embodiment of the invention, the fermentation broth or the intermediate yeast suspension or cream yeast derived from a fermentation broth is subjected to membrane filtration to obtain a further concentrated yeast cell suspension and a salt-containing effluent. Although any membrane filtration equipment is suitable for carrying out the process, preferred membrane filtration for cell separation is microfiltration. The salt-containing effluent may be concentrated, preferably by reverse osmosis. In a subsequent step, said concentrated salt-containing effluent is mixed with said concentrated cells. Although any concentration equipment is suitable for carrying out the process, preferred concentration equipment is a disc stack concentrator, a drum filter, or a filter press. Thus, by virtue of this embodiment, the salts present from the fermentation procedure are incorporated in the liquid yeast composition of the first aspect of the invention. In an alternative embodiment, additional salt or salt solution is added after the fermentation, before, during or after any of the subsequent process steps.

It will be obvious to the person skilled in the art that any of the processing aids defined hereinbefore and mentioned in the first aspect of the invention may be added before, during or after any step of the processes described in the embodiments of the second aspect. This applies also to the other compounds and/or gums referred to earlier in the first aspect of the invention.

The third aspect of the invention relates to a process for producing dough according to known methods characterized by adding a liquid yeast composition as defined in the first aspect of the present invention.

The fourth aspect of the invention relates to a process for producing a baked product from dough according to known methods characterized in that the dough is prepared by the process as defined in the third aspect of the present invention.

In a fifth aspect, the invention relates to a process for storing the yeast composition of the invention, i.e. a composition comprising 24-45% yeast (based on yeast dry matter) and more than 0.75% salt by maintaining the yeast composition at a temperature below 10° C. The term "storing" is defined herein as storage of the yeast composition of the invention in the period between its production at the yeast manufacturer's and its use at the bakers. This period may comprise storage at the yeast manufacturer before transport to the baker, the actual transport to the baker and subsequent storage before use by the baker as well as storage in the dosing equipment before and during the actual dosing at the baker's.

The yeast composition of the invention may be stored and transported in road tankers with volumes between 5,000 and 30,000 liters and subsequently transferred to fixed cream yeast tanks at the bakery. The yeast composition of the invention may also be stored and transported in smaller containers with volumes between 100 and 5000 liters such as disclosed in WO01/83309. Alternatively, the yeast composition may be stored and transported in smaller containers with a volume between 0.1 and 100 liters as disclosed in WO02/02428.

In a sixth aspect, the invention relates to the use of the liquid yeast composition of the invention, i.e. a composition comprising 24-45% yeast (based on yeast dry matter) and more than 0.75% salt for the manufacturing of a dough and/or a baked product from said dough.

FIG. 1 is a schematic representation of the traditional baker's yeast production process with fermentation (1), centrifugation (2), filtration (3), extrusion (4), water (5), salt solution (6), wastewater (7), cream yeast (8), and compressed yeast (9).

The invention is further illustrated by, but not limited to, the following Examples.

EXAMPLE 1

The Effect of Salt on the Intracellular Water Content of Yeast Cells

Different solid sodium chloride quantities were added to cream yeast with a 19.7% yeast dry matter content to give yeast suspensions 1-9 with different salt contents as indicated in Table 2. Yeast suspension 1 is cream yeast without any salt added.

The suspensions were stirred for 15 minutes after which 10 ml of each suspension was centrifuged for 10 minutes at 4000 rpm in a Hereaus centrifuge. The volumes and weights of pellets and corresponding supernatants were measured (second and third row in Table 2). The supernatants were analyzed for their salt content by measuring the chloride concentration. The pellets were analyzed for their total dry matter content using an infrared Sartorius balance. The yeast dry matter content was derived from the total dry matter content of the pellet by correcting for the salt present in the pellet. The amount of salt in the pellet is present in the extracellular water fraction of the pellet, which is ca 30% of the total pellet and has the same salt concentration as the supernatant.

It is clear from Table 2 that with increasing salt concentration, the volume and weight of the supernatant increases and that of the corresponding pellet decreases. However, the total amount of yeast dry matter (in grams) does not vary with the salt concentration: all the yeast dry matter is recovered in the pellets (average 2 grams). Since the volume of the pellets decreases, it means that the relative yeast dry matter content of the pellets increases significantly with increasing salt concentration. Hence it was concluded that the out flux of intracellular water increases with increasing salt concentration and therefore that the remaining amount of intracellular water decreases.

TABLE 2

| | Yeast suspension | | | | | | | | |
|---|---|---|---|---|---|---|---|---|---|
| | 1 | 2 | 3 | 4 | 5 | 6 | 7 | 8 | 9 |
| [NaCl] (wt %) | | | | | | | | | |
| suspension | 0.04 | 0.47 | 0.93 | 1.41 | 1.84 | 2.84 | 4.42 | 8.40 | 16.15 |
| supernatent supernatant | 0.09 | 1.05 | 1.51 | 2.29 | 2.92 | 4.24 | 6.46 | 10.73 | 20.27 |
| volume (ml) | 2.0 | 2.5 | 3.0 | 3.0 | 4.0 | 4.1 | 4.8 | 6.0 | 6.5 |
| weight (g) pellet | 2.13 | 2.62 | 3.06 | 3.41 | 3.69 | 4.33 | 5.19 | 6.17 | 7.00 |
| volume (ml) | 8.0 | 7.5 | 7.0 | 7.0 | 6.0 | 5.9 | 5.2 | 4.0 | 3.5 |
| weight (g) | 8.51 | 8.17 | 7.78 | 7.39 | 7.00 | 6.61 | 6.07 | 4.94 | 4.40 |
| yeast dry matter (g) | 2.16 | 2.13 | 2.14 | 2.12 | 2.09 | 2.15 | 2.21 | 2.03 | 1.99 |
| salt (g) | 0.00 | 0.03 | 0.04 | 0.05 | 0.06 | 0.08 | 0.12 | 0.16 | 0.27 |

TABLE 2-continued

| | Yeast suspension | | | | | | | | |
|---|---|---|---|---|---|---|---|---|---|
| | 1 | 2 | 3 | 4 | 5 | 6 | 7 | 8 | 9 |
| total dry matter (%) | 25.37 | 26.33 | 27.92 | 29.39 | 30.70 | 33.81 | 39.39 | 44.37 | 51.40 |
| yeast dry matter (%) | 25.34 | 26.02 | 27.47 | 28.70 | 29.82 | 32.54 | 36.45 | 41.15 | 45.32 |

EXAMPLE 2

The Effect of the Salt Content of a Yeast Suspension on the Leavening Activity

The leavening activity of the liquid yeast suspensions as described in Example 1 was measured in a lean dough test using a fermentometer system at 28° C. and expressed as milliliters $CO_2$. To 62.5 g of flour, 39 ml of water was added as well as 1.5 gram of standard cream yeast or a corresponding amount of the liquid yeast composition of the invention (based on yeast dry matter) and 1.25 g salt (or correspondingly less when the liquid yeast composition of the invention containing salt were tested). The mixture was mixed for 2.5 minutes. The gas production was measured after 10 minutes during a period of 165 minutes at 28° C. The leavening activity of yeast suspension 1 (i.e. cream yeast) was 100% by definition.

From the result in Table 3 it can be concluded that the presence of salt in the yeast suspension has no (negative) effect on the leavening activity of the yeast.

TABLE 3

| | Yeast suspension | | | | | | | | |
|---|---|---|---|---|---|---|---|---|---|
| | 1 | 2 | 3 | 4 | 5 | 6 | 7 | 8 | 9 |
| Leavening activity (%) | 100 | 100 | 100 | 100 | 99 | 99 | 100 | 101 | 99 |

EXAMPLE 3

The Effect of Storage Time of the Yeast Suspension on the Leavening Activity

The yeast suspensions of Example 1 were stored at 4° C. for a period up to 3 weeks. The leavening activity was measured as described in Example 2 at weekly intervals and compared with a reference sample without added salt (i.e. cream yeast). From the results in Table 4 it can be concluded that the relative stability of liquid yeast preparations does not decrease in time with increasing salt concentrations up to 2% (yeast suspensions 1-5, see Table 2) and that loss of leavening activity above salt concentrations of 2% is only minor.

TABLE 4

| Storage | Leavening activity (%) of yeast suspension | | | | | | | | |
|---|---|---|---|---|---|---|---|---|---|
| time (weeks) | 1 | 2 | 3 | 4 | 5 | 6 | 7 | 8 | 9 |
| 0 | 100 | 100 | 100 | 100 | 99 | 99 | 100 | 101 | 99 |
| 1 | 100 | 99 | 99 | 100 | 98 | 96 | 98 | 99 | 95 |
| 2 | 100 | 100 | 100 | 98 | 97 | 90 | 92 | 94 | 91 |
| 3 | 100 | 100 | 100 | 99 | 98 | 95 | 89 | 90 | 91 |

EXAMPLE 4

The Preparation of Liquid Yeast Compositions of the Invention Starting from Cream Yeast A liquid yeast composition was prepared by adding 106 grams of an aqueous solution of sodium chloride (25 wt %) to 400 grams cream yeast (19.9% yeast dry matter content). The salt concentration of this yeast suspension was therefore 5.2%. The out flow of intracellular water to the outside of the cells started immediately. The salted cream was centrifuged for 10 minutes at 4000 rpm in a Hereaus centrifuge resulting in a supernatant and a pellet. Liquid yeast compositions A, B and C were prepared by removing part of the supernatant and resuspending the pellet in the remaining part of the supernatant as indicated in Table 5.

TABLE 5

| Liquid yeast composition | Supernatant removed (%) | Yeast dry matter content |
|---|---|---|
| A | 70 | 24.9 |
| B | 84 | 31.2 |
| C | 92 | 33.0 |

EXAMPLE 5

The Preparation of a Liquid Yeast Composition of the Invention Starting from Compressed Yeast A liquid yeast preparation was prepared by mixing 500 g compressed yeast (27.9% yeast dry matter) with 14 g solid sodium chloride at 4° C. The out flow of intracellular water started immediately and the compressed yeast was liquefied. The final liquid yeast composition contained 2.7% NaCl and had a yeast dry matter content of 27%.

EXAMPLE 6

The Preparation of a Liquid Yeast Composition of the Invention Starting from Fermentation Broth Fermentation broth with a yeast dry matter content of approximately 7 wt %, was obtained from a yeast fermentation that was carried out according to known methods. The broth was centrifuged as described hereinbefore. The pellet was washed twice by resuspending in a washing liquor consisting of an aqueous solution of sodium chloride (4 wt %) and centrifugation. After the last centrifugation step, only part of the supernatant was removed such that a liquid yeast composition with a yeast dry matter of 27% was obtained.

EXAMPLE 7

The Sedimentation Behavior of the Yeast Composition of the Invention

A liquid yeast preparation as described in Example 4 was stored at 4° C. for 6 weeks in comparison with a cream yeast product. The sedimentation behavior was monitored by measuring the volume percentage of clear liquid that was formed during storage. From the result in Table 6 it can be concluded that sedimentation of the liquid yeast composition of the invention (Composition C as prepared in Example 4) is reduced in comparison with cream yeast.

TABLE 6

| | Clear liquid formed (% of total volume) | |
|---|---|---|
| Storage time (days) | Liquid yeast composition C | cream yeast |
| 0 | 0 | 0 |
| 4 | 5 | 15 |
| 10 | 10 | 32 |
| 18 | 12 | 34 |
| 25 | 12 | 33 |
| 31 | 13 | 34 |
| 40 | 15 | 34 |
| 45 | 15 | 37 |

EXAMPLE 8

The Preparation of Liquid Yeast Compositions by Centrifugation on Large Scale To 1000 liters of cream yeast (21.7% yeast dry matter content) solid salt was added to initially 2 wt %. The salt-containing cream was concentrated by centrifugation using a nozzle separator (Westfalia NA 7). A sample of the liquid pellet was taken for analysis (liquid yeast composition D). After recombination of the liquid pellet and the supernatant, additional salt was added to a final concentration of 4%; a liquid yeast composition sample E was collected as described before for D. After again recombination of the liquid pellet and the supernatant, additional salt was added to a final concentration of 6%; a liquid yeast composition sample F was collected as described before for D en E. Finally, approximately 650 liters of liquid yeast composition F was obtained having a yeast dry matter of 32.8%. Table 7 summarizes the results of the various analyses.

TABLE 7

| NaCl added (wt %) | Liquid yeast preparation | Yeast dry matter (%) | Leavening activity (%) |
|---|---|---|---|
| 0 | cream yeast | 21.7 | 100 |
| 2 | D | 27.6 | 102 |
| 4 | E | 30.1 | 101 |
| 6 | F | 32.8 | 96 |

EXAMPLE 9

The Preparation of a Liquid Yeast Composition of the Invention by Membrane Filtration on Large Scale To 150 liters of cream yeast (20% yeast dry matter), 8.6 kg solid sodium chloride was added. The salted cream yeast was further concentrated by membrane filtration (Ecoceramics; poresize 0.5 um; 0.66 m²) to a liquid yeast composition of 28% yeast dry matter. The dead space of the membrane filtration equipment caused a dilution of the salted cream yeast with approximately 20 liters of water. The membrane filtration (micro filtration) was carried out in a batch-wise set-up. The retentate was cooled in order to keep the temperature below 4° C. in the available equipment.

EXAMPLE 10

The Baking Performance of Liquid Yeast Compositions of the Invention

Liquid yeast compositions were prepared by adding a 25 wt % solution of sodium chloride to 500 grams of cream yeast having a yeast dry matter content of 21.5% yielding salted cream yeasts with a salt content ranging from 1.9 to 5.7 wt %. The salted cream yeasts were centrifuged to give the pellets as indicated in Table 8. The liquid yeast compositions of the invention G, H, J and K were obtained by resuspending the pellets in the quantity of supernatant as indicated in Table 8. All experiments were carried out at 4° C. The baking performance of the liquid yeast compositions was tested in a Dutch tin bread-baking test using the recipe depicted below.

| | |
|---|---|
| Flour | 3500 g |
| Water | 1905 g |
| Yeast (based on 30% yeast dry matter content) | 77 g |
| Salt | 70 g |
| Ascorbic acid (3.5 g/l) | 40 g |
| Amylase (Fermizyme P200 3.5 g/l - DSM, The Netherlands) | 25 g |
| Hemicellulase (Fermizyme HS2000 3.5 g/l - DSM, The Netherlands) | 60 g |

The amount of yeast used in each baking test was corrected for the yeast dry matter content of the liquid yeast composition such that in all baking tests the same amount of yeast dry matter was used. The results in Table 8 show that the liquid yeast compositions of the invention (G, H, J and K) have a baking performance: which is as good as the cream yeast that they were made from.

TABLE 8

| Liquid yeast composition | salt content of salted cream (wt %) | Pellet (g) | Supernatant added (g) | yeast dry matter content | Bread volume (ml) |
|---|---|---|---|---|---|
| cream yeast | no addition | 329 | 82 | 21.5 | 3713 |
| G | 1.9 | 301 | 75 | 25.9 | 3580 |
| H | 3.3 | 264 | 65 | 27.8 | 3736 |
| J | 4.5 | 236 | 59 | 29.3 | 3720 |
| K | 5.7 | 215 | 53 | 30.4 | 3712 |

EXAMPLE 11

Biological Stability as a Function of the Storage Temperature

To 500 g cream yeast with a yeast dry matter of 20.3%, 148 gram of a 25-wt % aqueous solution of sodium chloride was added. The salted cream was centrifuged for 10 minutes at 4000 rpm in a Beckmann centrifuge at 4° C. The pellet was resuspended in 53.2 gram of the supernatant to give a liquid yeast composition with a yeast dry matter content of 30.4%.

The biological stability (measured as the residual leavening activity) was measured by storing the liquid yeast composition at 4° C., 8° C. and 15° C. The leavening activity was measured in the lean dough test as described in Example 2.

Table 9 shows that at temperatures below 10° C., the liquid yeast composition of the invention was very stable and lost almost no leavening activity in comparison with a storage temperature of 15° C. At 4° C. and 8° C., it behaved essentially the same as normal cream yeast (i.e. without the salt added) whereas the latter was much more stable at 15° C. (85% residual leavening activity after 3 weeks).

TABLE 9

| Storage time (days) | Residual leavening activity | | |
|---|---|---|---|
| | Storage temperature | | |
| | 4° C. | 8° C. | 15° C. |
| 0 | 100% | 100% | 100% |
| 7 | 98% | 97% | 92% |
| 14 | 100% | 97% | 67% |
| 21 | 97% | 87% | 34% |

The invention claimed is:

1. A composition comprising between 24% and 45% yeast (based on yeast dry matter content) wherein the composition contains more than 0.75% salt, wherein the amount of salt in the composition is adjusted relative to the yeast dry matter content so that the composition is liquid, and wherein the composition is biologically stable in the absence of added sugar when maintained at a temperature below 10° C.

2. The composition of claim 1 further comprising one or more processing aids.

3. The composition of claim 2 wherein the processing aids are chemical additives and/or enzymes.

4. The composition of claim 3 wherein the chemical additives are selected from the group consisting of oxidizing agents, reducing agents, emulsifiers, bile salts, and the enzymes are selected from the group consisting of starch degrading enzymes, arabinoxylan degrading enzymes, hemicellulose degrading enzymes, cellulose degrading enzymes, oxidizing enzymes, fatty material splitting enzymes and protein degrading enzymes.

5. The composition of claim 1 further comprising one or more gums.

6. A process for the production of a composition as defined in claim 1 comprising:
   a) preparing a yeast suspension with a yeast dry matter content between 3% and 23%;
   b) concentrating the yeast suspension of step a) to a yeast composition with a yeast dry matter content higher than 23%;
   c) adding solid salt or a salt solution during or after step a) or step b); and
   d) cooling the yeast suspension or composition before, during or after step c) to a temperature below 10° C.

7. The process of claim 6 which further includes adding one or more processing aids during or after any of steps a), b) or c).

8. A process for the production of a composition as defined in claim 1 comprising:
   a) performing membrane filtration of a yeast-containing fermentation broth or of cream yeast to obtain concentrated cells and salt-containing effluent;
   b) concentrating the salt-containing effluent of step a) and
   c) mixing said effluent with the concentrated cells of step a).

9. The process of claim 8 which further includes adding one or more processing aids during or after any of steps a), b), and/or c).

10. The process of claim 8, which further includes adding salt or a salt solution to the yeast-containing fermentation broth during or after fermentation.

11. A process for producing dough which comprises adding to additional dough ingredients a liquid yeast composition as defined in claim 1.

12. A process for producing a baked product from a dough which method comprises baking a dough prepared by the process as defined in claim 11.

13. A process for storing a liquid yeast composition comprising between 24% and 45% yeast (based on yeast dry matter) and more than 0.75% salt which process comprises maintaining the liquid yeast composition at a temperature below 10° C.

* * * * *